(12) United States Patent
Golubev et al.

(10) Patent No.: US 7,077,335 B2
(45) Date of Patent: Jul. 18, 2006

(54) DEVICE FOR AROMATIZING A GAS MEDIUM

(75) Inventors: Anatoly Viktorovich Golubev, Moscow (RU); Mikhail Alexandrovich Gluyansky, Varshavskoe shosse, 128-1-331, Moscow (RU) 113587; Evgeny Gennadievich Krasheninnixov, Khimki (RU); Vladimir Lomberg, Ha Galil, 88/17, Ganei Tigwa (IL); Boris Vasilevich Potapkin, Moscow (RU); Danill Alexandrovich Rybak, Moscow (RU)

(73) Assignees: Mikhail Alexandrovich Gluyansky, Moscow (RU); Vladimir Lomberg, Ganei Tikva (IL)

( * ) Notice: Subject to any disclaimer, the term of this patent is extended or adjusted under 35 U.S.C. 154(b) by 0 days.

(21) Appl. No.: 10/492,902

(22) PCT Filed: Oct. 17, 2001

(86) PCT No.: PCT/RU01/00426

§ 371 (c)(1),
(2), (4) Date: Apr. 16, 2004

(87) PCT Pub. No.: WO02/40377

PCT Pub. Date: May 23, 2002

(65) Prior Publication Data

US 2005/0072857 A1    Apr. 7, 2005

(30) Foreign Application Priority Data

Nov. 16, 2000    (RU)    ............................ 2000128475

(51) Int. Cl.
*A01G 25/02* (2006.01)
*B05B 1/08* (2006.01)
*A62C 13/62* (2006.01)

(52) U.S. Cl. ............... 239/66; 239/102.2; 239/304; 239/308; 239/266; 239/69; 261/30

(58) Field of Classification Search .......... 239/66–70, 239/102.1, 102.2, 304, 308, 266–269, 318; 128/200.13, 200.16; 261/30
See application file for complete search history.

(56) References Cited

U.S. PATENT DOCUMENTS 3,044,276 A * 7/1962 Kauten ................. 62/311

(Continued)

FOREIGN PATENT DOCUMENTS

FR    2659854    9/1991

(Continued)

*Primary Examiner*—David A. Scherbel
*Assistant Examiner*—Seth Barney
(74) *Attorney, Agent, or Firm*—Paul & Paul

(57) ABSTRACT

The inventive device for aromatizing a gas medium comprises a chamber provided with a flow booster for mixing the gas medium with aromatic fumes. Said fumes are delivered to the chamber by a dispenser which is embodied in the form of a reservoir containing a liquid aromatic substance. The dispenser is provided with a system of nozzles for supplying the aromatic substances to the mixing chamber. The supply of the substance is carried out by producing pressure pulses inside the chamber. Said pulses occur as a result of a pulse operation of actuating elements which are arranged in the chamber and embodied in the form of thermistors, stricting elements and controlled commutator. Said actuating elements are controlled by a field programmed logic array which is also controlled by a panel or a computer and programmed in relation to a value, duration and repetition rate of voltage pulses coming to actuating elements. The diameters of the nozzles range from 10 to 70 μm, the distance therebetween being less than 50 μm.

18 Claims, 2 Drawing Sheets

U.S. PATENT DOCUMENTS

| | | |
|---|---|---|
| 3,970,250 A | 7/1976 | Drews |
| 4,702,418 A * | 10/1987 | Carter et al. ................ 239/101 |
| 5,011,632 A * | 4/1991 | Yano et al. .................... 261/81 |
| 5,025,962 A | 6/1991 | Renfro |
| 5,152,457 A * | 10/1992 | Burwell et al. ........... 239/102.2 |
| 5,483,953 A * | 1/1996 | Cooper .................. 128/200.22 |
| 6,357,671 B1 * | 3/2002 | Cewers .................... 239/102.2 |
| 6,439,474 B1 * | 8/2002 | Denen ..................... 239/102.2 |
| 6,554,203 B1 * | 4/2003 | Hess et al. ..................... 239/69 |
| 6,651,650 B1 * | 11/2003 | Yamamoto et al. .... 128/200.16 |
| 6,702,196 B1 * | 3/2004 | Ohnishi et al. .......... 239/102.2 |
| 6,712,287 B1 * | 3/2004 | Le Pesant et al. ............ 239/67 |
| 6,726,186 B1 * | 4/2004 | Gaaloul et al. ................ 261/81 |
| 6,837,445 B1 * | 1/2005 | Tsai ........................ 239/102.2 |

FOREIGN PATENT DOCUMENTS

| | | |
|---|---|---|
| FR | 2667508 | 4/1992 |
| SU | 1808335 | 4/1993 |

* cited by examiner

DEVICE FOR AROMATIZING A GAS MEDIUM

FIELD OF THE INVENTION

The present invention relates to devices for producing aromatized air flows, and is aimed at establishing a more complete pattern of a surrounding world when it is used in the aggregate with other multimedia means. The present invention may be used in medicine and also in pharmaceutical, food, chemical and perfume industries, where it is necessary to reproduce the known odors and produce the new ones, and also to reproduce various climatic conditions. The invention is suited for producing gaseous mixtures with a specified content of constituents, for example, checking mixtures, etc.

BACKGROUND OF THE INVENTION

There have been known a process and a device therefor, comprising a convective diffusion of an aromatizer carried out into the air from the surface of evaporation. To carry out evaporation, the aromatizer is heated by the hot water (see, for example, USSR Inventor's Certificate 1,775,119, Int. Cl. A61L 9/00, dated 1990).

The drawbacks with the known technical solution consist in duration of going into the operating mode (heating of water to 60–95° C.), impossibility to produce several odors and impossibility to perform the synthesis of a new odor.

The closest prior art has been disclosed in a device for aromatizing a gaseous medium containing a chamber for mixing the gaseous medium with vapors of an aromatizer, said chamber is provided with inlet and outlet pipes; at least one aromatizer dispenser connected to the mixing chamber, said dispenser containing a vessel for the aromatizer; actuating elements connected with a power supply; a unit for controlling the operation of the device; a gaseous medium flow booster provided with a control unit, for circulating the gaseous medium through the mixing chamber (see, USSR Inventor's Certificate 1,808,335 A1, Int. Cl. A61L 9/00, dated 1989). In this prior art, an actuating element is a laser that travels from one section containing the aromatizer to another. With the change in an odor, it is necessary to ventilate a housing and use a special device to neutralize the odor. The drawbacks with the known device are as follows:

1. Aromatic substances are arranged in open sections. A vapor pressure of a majority of solid and all liquid aromatic substances is rather high. Therefore, even without heating of the samples by a laser, the air entering the working chamber will be enriched with vapors of aromatic substances. At the outlet of the device, the air will always contain a quantity of vapors of the aromatizer.

2. An evaporation rate of the aromatizer on heating of the sample depends on its temperature. In turn, a maximum heating temperature is confined to the temperature values with which destruction of a material begins. Consequently, a vapor quantity that may be admitted into the airflow per unit time is also limited.

3. The processes for heating and vaporizing the aromatizer are rather slow. Consequently this device may only be used in cases where a fast response of the device to a controlling signal or a fast replacement of one odor with another are not needed.

4. Moving elements (a laser) are present in the device. The availability of the moving elements shortens the service life of the device and invites additional works as regards the device maintenance.

5. The device makes use of an odor neutralizer. It is known that in order to neutralize an odor of each aromatic substance, a variety of absorbents are used. Therefore, in order to handle different aromatic substances, there is a need to develop a very complicated device for neutralizing an odor.

6. The laser may vaporize one aromatizer only; that is to say the device prevents mixed odors from being produced.

SUMMARY OF THE INVENTION

It is an object of the present invention to provide a device that overcomes the above described drawbacks and enables one to change the odors quickly, alter their intensity, obtain a predetermined mixture of odors, expand the range of concentration of an aromatizing substance per unit This object is solved in accordance with the present invention by This object is solved in accordance with the present invention by means of a device for aromatizing a gaseous medium containing a chamber for mixing a gaseous medium with vapors of an aromatizer, said chamber is provided with inlet and outlet pipes for circulating the gaseous medium; at least one aromatizer dispenser connected to the mixing chamber, said dispenser containing a vessel for the aromatizer and an actuating element to be connected to a power supply; a unit for controlling the operation of the device; and a gaseous medium flow booster for circulating the gaseous medium through the mixing chamber. In accordance with the present invention the aromatizer dispenser additionally comprises a reservoir connected to the vessel for a liquid aromatizer. In addition, a wall of the aromatizer has, at least, one nozzle for injecting the aromatizer into the mixing chamber, and the actuating element made to create pressure pulses in the reservoir filled with the aromatizer is arranged inside the reservoir on its wall fabricated from an insulating material.

This technical solution allows alteration, over a wide range, of a quantity of the aromatizer coming to the mixing chamber per unit time. Change in the quantity of the aromatizer coming to the mixing chamber is achieved by altering a frequency, duration and amplitude of pulses supplied to the actuating elements of the dispenser and also by altering the number of the aromatizer nozzles that operate concurrently. The device makes it possible to produce various concentrations of aromatizers in the air and alter a concentration and a flow rate of the air by a signal from a control unit. Saturation of the airflow in the mixing chamber with the aromatizer takes place within hundredths of second (the time of vaporization of droplets) after a control signal was supplied to the device. Termination of the aromatizer delivery to the working chamber takes place within hundredths of second after a corresponding signal was supplied to the device. The device makes possible mixed odors. The mixing of several odors takes place during a simultaneous operation of several dispensers. Replacement of one odor with another takes place in a time of changing the air in the working chamber. With the specified flow rates of the air through the working chamber, this time shall not exceed 5 seconds. The device allows operation with a variety of aromatic substances, since a wide range of solvents may be used to produce solutions of aromatic substances.

A control unit may be connected to actuating elements through a programmed logic unit. The programmed logic unit may be embodied in the form of a controller provided with a multiplexing unit of controlling the parameters of voltage pulses.

There may be several actuating elements, as in the case with nozzles; the said actuating elements may be arranged opposite the nozzles, along the axis of the nozzles or with a shift with respect to the axes of the nozzles. It is possible to arrange the nozzles partially under the first variant and partially under the second variant. The choice of a particular variant of arranging the actuating elements and nozzles is defined by physico-mechanical properties of a liquid aromatizer used.

According to the present invention, the elements intended to produce pressure pulses in the dispenser chamber and to supply the aromatizer through the nozzles to the mixing chamber are made in the form of stricting and/or resistive elements. Piezoelectric crystals may be used as stricting elements and thermistors—as resistive elements. When using dispensers of thermistors as the actuating elements, the heating of the aromatizer occurs only in a time of a pulse feeding the actuating element (in the neighborhood of 5 μsec). Dispensers with the actuating elements made in the form of resistors, for instance thermistors, may be applied in case where it is necessary to reduce the cost of the device.

It was established that the best results were achieved when the nozzles were embodied in the form of orifices with the diameters in the reservoir wall ranging from 10 to 70 μm. This enables to produce, in the process for dispensing, rather small droplets which have an opportunity to vaporize in the flow of a gaseous medium before the aromatizer droplets ejected from the nozzles could reach the wall of the mixing chamber. It is determined that the best operation of the nozzles is ensured by the choice of a distance therebetween being no less than 50 μm.

As a liquid aromatizer, use is made of an aromatizing substance itself or a solution of the aromatizer in a liquid solvent that does not affect an organoleptical perception of an odor of the aromatizer. When using a solvent, it is important that a gaseous medium has a reduced content of the solvent vapors, because an increased content of these vapors retards vaporization of the aromatizer solution. For instance, when the air saturated with the water vapors is used as a gaseous medium along with the use of an aromatizer aqueous solution, vaporization of the aromatizer droplets may not occur at all. In this case a gaseous medium flow booster must be provided with a device for a gaseous medium preparation, which envisages the use of a water absorber (air desiccation). The device for the gaseous medium preparation may be provided, should the need arise, with a heater (cooler) of the gaseous medium, thus enabling expansion of a set of organoleptical perceptions. To control the operation of the device for the gaseous medium preparation, it may be actuated from a programmed logic unit.

Depending on the function of the present invention, a unit for controlling the operation of the device is used in the form of a special panel, or a computer connected to the input of a programmed logic array through standard computer ports.

DESCRIPTION

Figure 1:
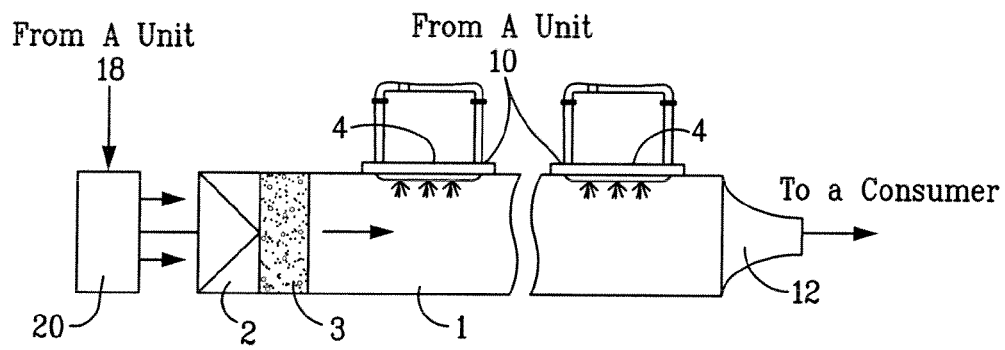
FIG. 1 is a schematic general view of a device for aromatizing a gaseous medium.
Figure 2:
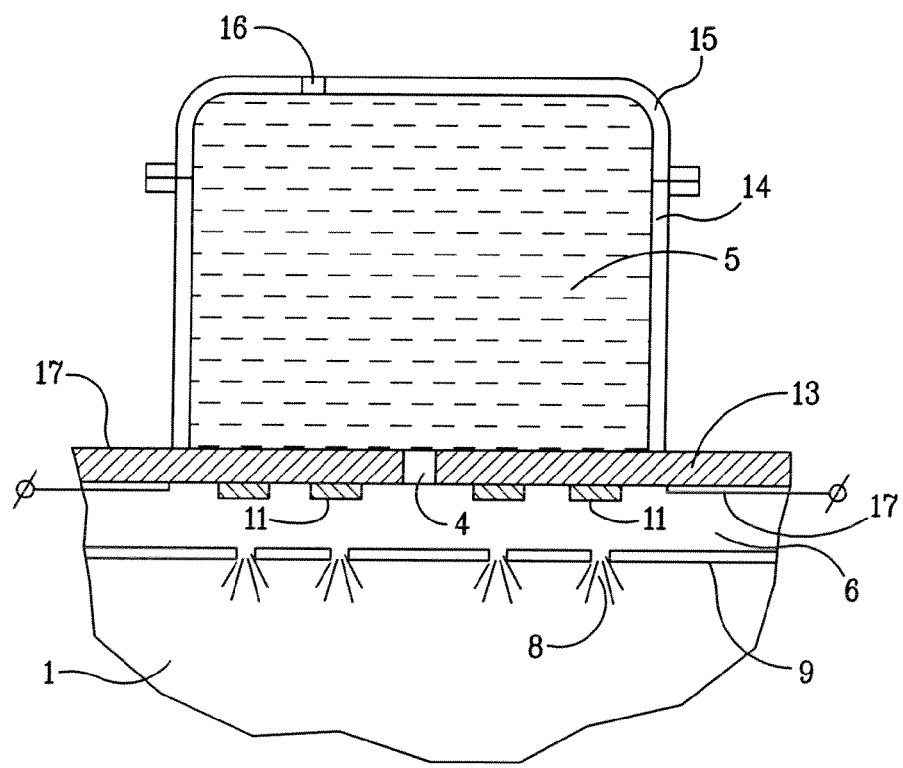
FIG. 2 illustrates an aromatizer dispenser.
Figure 3:
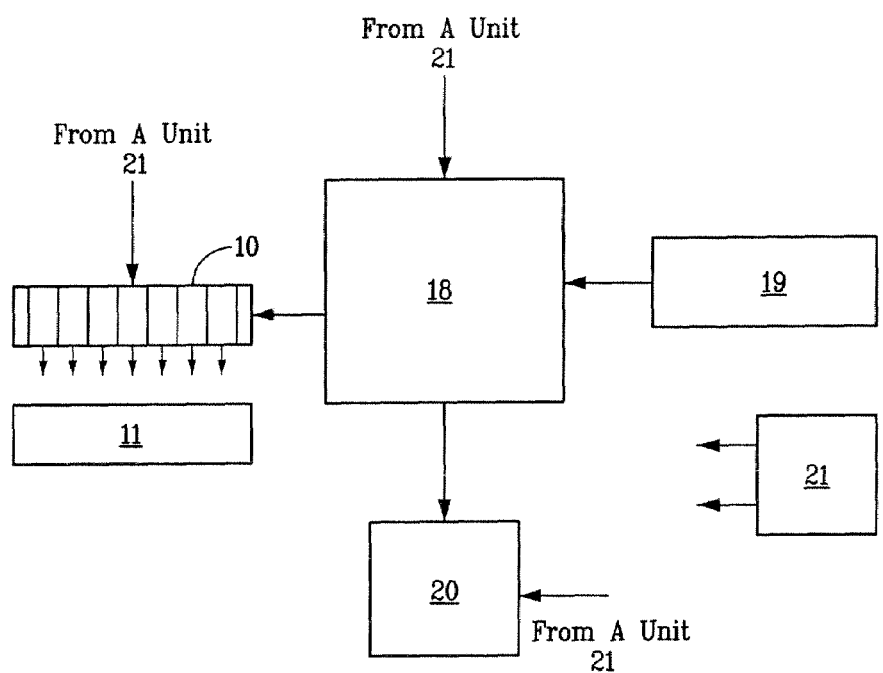
FIG. 3 shows a block diagram of the process for controlling the operation of an aromatization device.

The accomplishment of a device for eromatizing the air suggests that its operation is possible in combination with a computer. The device comprises a chamber 1 for mixing a gaseous medium with an aromatizer. The chamber is tightly Joined to a booster 2 for circulating the gaseous medium, in this case, the air. The air coming to the chamber passes through an air preparation unit 3, where the air is desiccated from vapors of atmospheric moisture. Dispensers 4 of aromatic substances are connected to the mixing chamber 1. Each dispenser is provided with a vessel S for storing an aromatic substance. A dispenser reservoir 6 is filled with an aromatizer solution coming from the vessel S through an orifice 7. Aromatizer solutions arrive at the chamber 1 through nozzles 8 made in a wall 9 of the dispenser reservoir. An outlet of the nozzles 8 is arranged within the chamber 1. A full flow rate of the aromatizer solution is defined by the flow rate through each nozzle 8 and by the quantity of nozzles operating concurrently. A commutator 10 regulates the quantity of nozzles operating concurrently. Actuating elements 11 of the dispenser regulates a solution flow rate through each nozzle. Saturation of the prepared air with aromatic substances takes place during vaporization of aromatizer solutions in the working chamber 1. The air saturated with an aromatizer comes to a consumer through an outlet pipe 12. On termination of the supply of the aromatizer solution to the working chamber 1, the aromatizer is removed and, accordingly, an odor is neutralized. When several dispensers 4 operate concurrently, a consumer receives a mixture of odors. The dispenser 4 of aromatic substances (FIG. 2) contains a plate 13 made of an insulating material, said plate serving one of the walls of the reservoir 6 with its inner side having actuating elements 11 of the dispenser 4 (which are applied, for example, onto the surface of the plate 13). As shown in FIG. 2. each of the nozzles 7 is regulated by a corresponding actuating element 11.

The said elements are intended to produce pressure pulses in the reservoir 6 of the dispenser and to supply the aromatizer through the nozzles. The vessel 5 for storing aromatic substances comprises a housing 14 tightly joined to a cover 15 of this vessel, in the cover 15 of the vessel there is an opening 16 to connect the insides of the vessel with the atmosphere. Current supply plates 17 arranged on the plate 13 serve to electrically connect the actuating elements 11 of the dispenser 4 to the commutator 10 with its controlling input connected to a commutating output of a programmed logic unit (PLU) 18. The actuating elements 11 are arranged along the axis of the nozzles 8 or with a shift in respect of these axes. A combined arrangement is also possible (with a part arranging along the axis of the nozzles and a part arranging with a shift in respect of these axes). The actuating elements 11 are striding and/or resistive elements, for example, piezoelectric crystals or thermistors The best characteristics are observed when the nozzles are accomplished with the diameter ranging from 10 to 70 μm and the distance between separate nozzles being no less than 50 μm. The PLU is made programmed in relation to parameters of voltage pulses coming to the actuating elements 11, and it has an input for connection to a unit 19 for controlling the operation of the device for aromatization. The PLU has a second input connected to a controlling input of a unit 20 for controlling an air flow rate booster 2, and a third input (not shown in the drawing) connected to a controlling input (not shown in the drawing) of an air preparation unit 3. In this instance, the PLU is made programmed in relation to a value, duration and repetition rate of voltage pulses coming to the actuating elements it The PLU may be embodied in the form of a controller provided with a multiplexing unit for controlling parameters of voltage pulses coming to the actuating elements. In the case under consideration, the unit 19 for controlling the operation of the device is embodied in the form of a computer connected to the PLU input through standard ports. The unit 19 may also be embodied in the form of a specialized control panel. The device according to the present invention is provided with an electric power unit 21 connected to the PLU, the commutator and the unit 20.

The operation of the claimed device is explained by the following examples of embodying and using the present invention.

EXAMPLE 1

A dispenser is filled with a 1% solution of a jasmine flavor in ethyl alcohol. Use is made of the dispenser with 48 nozzles arranged in four rows, 12 nozzles in each row; the diameter of the nozzles is 30 μm, and the distance between the nozzles is 200 μm. Piezoelectric crystals are arranged on an insulating plate. Each piezoelectric crystal is located along the axis of its own nozzle. When applying an electric pulse to the piezoelectric crystal, pressure jumps arise within a dispenser chamber, with droplets of the solution formed at a cut of the nozzles. Control of the device is carried out from a control unit designed purposely. In the working chamber, airflow is produced with a flow rate being 500 n*cm$^3$/sec and a linear velocity being 20 cm/sec. The solution comes to the airflow in the form of droplets having 30–45 μm in size. The voltage across a piezoelectric crystal is 24 V, a repetition rate of pulses is 10 kHz, and a pulse duration is 4 μsec. A total flow rate of the solution amounts to $10^{-3}$ g/sec. All droplets are vaporized at a distance of 2 cm from the outlet of the nozzles. Concentration of an aromatic substance in the airflow at the outlet of the working chamber accounts for $10^{14}$ $cm^{-3}$. A jasmine odor is perceived in the airflow at the outlet of the working chamber. Following the tapping off of the voltage from the piezoelectric crystals, the odor vanishes within 3–4 seconds.

EXAMPLE 2

A dispenser is filled with a 1% solution of an aloe flavor in ethyl alcohol. Use is made of the dispenser with 48 nozzles; the diameter of the nozzles is 30 μm, and the distance between the nozzles is 200 μm. Piezoelectric crystals serve as actuating elements of the dispenser. Control of the device is carried out through a computer COM-port. In the working chamber, airflow is produced with a flow rate being 2,500 $cm^3$/sec and a linear velocity being 100 cm/sec. The solution is supplied to the airflow in the form of droplets having 30–45 μm in size. A total flow rate of the solution amounts to $10^{-3}$ g/sec. All droplets are vaporized at a distance of 1.5 cm from the outlet of the nozzles. Concentration of an aromatic substance in the airflow accounts for $2*10^{13}$ $cm^{-3}$. An aloe odor is perceived at the outlet of the working chamber. Following the tapping off of the voltage from the piezoelectric crystals, the odor vanishes within 2–3 seconds.

EXAMPLE 3

A dispenser is filled with a 1% solution of a camomile flavor in ethyl alcohol. Use is made of the dispenser with 12 nozzles; the diameter of the nozzles is 65 μm, and the distance between the nozzles is 100 μm. Resistors serve as actuating elements of the dispenser. The resistors are arranged along the axes of the nozzles. Control of the device is carried out through a computer COM-port. In the working chamber, airflow is produced with a flow rate being 500 $cm^3$/sec and a linear velocity being 20 cm/sec. The solution is supplied to the airflow in the form of droplets having 65–70 μm in size. A total flow rate of the solution amounts to $10^{-3}$ g/sec. All droplets are vaporized at a distance of 5 cm from the outlet of the nozzles. Concentration of an aromatic substance in the airflow accounts for $10^{14}$ $cm^{-3}$. A camomile odor is perceived at the outlet of the working chamber. Following the tapping off of the voltage from the actuating elements of the dispenser, the odor vanishes within 3–4 seconds.

EXAMPLE 4

A dispenser is filled with a 1% solution of a brier flavor in distilled water. Use is made of the dispenser with 12 nozzles; the diameter of the nozzles is 30 μm. Piezoelectric crystals serve as actuating elements of the dispenser. Control of the device is carried out from a control unit designed purposely. In the working chamber, airflow is produced with a flow rate being 500 $cm^3$/sec and a linear velocity being 20 cm/sec. The solution comes to the airflow in the form of droplets having 30–45 μm in size. A total flow rate of the solution amounts to $10^{-3}$ g/sec. All droplets are vaporized at a distance of 2.5 cm from the outlet of the nozzles. Concentration of an aromatic substance in the airflow accounts for $10^{14}$ $cm^{-3}$. A brier odor is perceived at the outlet of the working chamber. Following the tapping off of the voltage from a piezocell, the odor vanishes within 3–4 seconds.

EXAMPLE 5

A dispenser is filled with a 10% solution of a pine ethereal oil in isopropyl alcohol. Use is made of the dispenser with 12nozzles; the diameter of the nozzles is 40 μm, and the distance between the nozzles is 220 μm. Resistors serve as actuating elements of the dispenser. The actuating elements are shifted by 20 μm with respect to longitudinal axes of the nozzles. In the working chamber, airflow is produced with a flow rate being 500 $cm^3$/sec and a linear velocity being 20 cm/sec. The solution comes to the airflow in the form of droplets having 40–45 μm in size. A total flow rate of the solution amounts to $10^{-4}$ g/sec. All droplets are vaporized at a distance of 3 cm from the outlet of the nozzles. Concentration of an aromatic substance in the airflow amounts to $10^{13}$ $cm^{-3}$. A pine odor is perceived at the outlet of the working chamber. Following the tapping off of the voltage from the actuating elements of the dispenser, the odor vanishes within 4–5 seconds.

Industrial Application

As appears from the examples, above, the proposed device enables to produce a wide range of odors in a specified volume. The emergence of an individual or synthesized odor is found within 5–10 seconds after an electrical voltage was applied to the actuating elements of the dispenser, whereas the elimination of an odor occurs within 2–5 seconds after an electrical voltage was removed from the actuating elements of the dispenser. The use of dispensers with the nozzles having the diameter less than 70 μm and the choice of parameters of supplying the actuating elements of the dispenser make it possible to produce droplets of solutions with dimensions not exceeding 70 μm. Vaporization of the droplets having such dimensions occurs in the working chamber in the range from 100 $cm^3$/sec to 2,500 $cm^3$/sec and the air flow rates in the working chamber in the range from 20 cm/sec to 500 cm/sec. The application of such a process for dispensing solutions of aromatizers enables to minimize dimensions of the device. The application of dispensers with different quantity of nozzles and/or the application of different quantity of nozzles in each dispenser allows alteration of the flow rate of solutions to be introduced into the working chamber over a wide range ($10^{-1}_{5-10}$ g/sec), which, in turn, enables to alter the concentration of aromatic substances in the air flow passing through the working chamber over a wide range ($10^{11-10^{16}}$ cm$^{-3}$). The application of dispensers with different quantity of nozzles makes it possible to use aromatic substances with different limits of sensibility as to odors in the range from $10^{12}$ to $10^{15}$ cm$^{-3}$. The device makes it possible to produce a wide range of individual or synthesized odors in a predetermined volume ~1 m$^3$ for an individual user. For collective users, an odor may be produced in large volumes when using several devices operating concurrently. The proposed device allows the production of essentially any individual odor and creation of new odors based on the synthesis of the simplest aromatic substances.

Although the present invention has been described with reference to a preferred embodiment, the invention is not limited to the details thereof, and various changes and modifications obvious to one skilled in the art to which the invention pertains are deemed to be within the spirit, scope and contemplation of the invention as further defined in the appended claims.

What is claimed is:

1. A device for aromatizing a gaseous medium, the device comprising:
   (a) a mixing chamber;
   (b) a booster for circulating a gaseous medium through the mixing chamber,
   (c) at least one dispenser for providing aromatizer fumes to the mixing chamber, the at least one dispenser being connected to the mixing chamber, the at least one dispenser including:
   (1) a storage vessel for an aromatizer solution;
   (2) a reservoir for the aromatizer solution, the reservoir having:
      (i) a first wall made of an insulating material, the reservoir being connected to the storage vessel through the first wall;
      (ii) more than one actuating element for producing pressure pulses in the aromatizer solution in the reservoir. said more than one actuating element being located on the first wall and being connectable to a power supply;
      (iii) a second wall;
      (iv) more than one nozzle in the second wall for injecting the aromatizer solution into the mixing chamber from the reservoir to produce aromatizer fumes, the flow rate of the aromatizer solution through each of the more than one nozzles being regulated by a corresponding actuating element of the more than one actuating elements; and
   (d) a control unit.

2. A device according to claim 1, the device additionally comprising:
   a commutator having a controlling input and outputs for controlling respective actuating elements, the actuating elements being connected to the commutator;
   the control unit having a first output and a second output, the first output being connected to the input of the commutator for controlling the commutator, the second output being connected to the booster for controlling the booster.

3. A device according to claim 2, the commutator providing voltage pulses to the actuating elements, the control unit being programmed to control the value, duration and repetition rate of the voltage pulses.

4. A device according to claim 1, each of the more than one nozzles having a respective axis, each of the more than one actuating elements being arranged opposite the corresponding nozzle and along the respective nozzle axis.

5. A device according to claim 1, each of the more than one nozzles having a respective axis, each of the more than one actuating elements being arranged opposite the corresponding nozzle and with a shift with respect to the respective nozzle axis.

6. A device according to claim 1 having at least two nozzles having respective axes and at least two respective actuating elements. the at least two nozzles being arranged opposite respective actuating elements, at least one actuating element being arranged along the respective nozzle axis, and at least one actuating element being arranged with a shift with respect to the respective nozzle axis.

7. A device according to claim 1, the diameters of the nozzles ranging from 10 to 70 µm.

8. A device according to claim 1, the distance between separate nozzles being no less than 50 µm.

9. A device according to claim 1 further comprising an air preparation unit.

10. A device according to claim 2 further comprising an air preparation unit, the control unit having a third output for controlling the air preparation unit.

11. A device according to claim 1 further comprising a computer connected to an input of the control unit for controlling the operation of the device.

12. A device according to claim 1 wherein the at least one actuating element is selected from the group consisting of "stricting" elements and resistive elements.

13. A device according to claim 12 wherein the "stricting" elements are piezoelectric crystais.

14. A device according to claim 12 wherein the resistive elements are thermistors.

15. A dispenser for providing aromatizer fumes, the dispenser including:
   (a) a storage vessel for an aromatizer solution;
   (b) a reservoir for the aromatizer solution, the reservoir having:
      (1) a first wall;
      more than one plezoelectric crystal in the reservoir for producing pressure pulses in the aromatizer solution in the reservoir, the more than one piezoelectric crystal being located on the first wall;
      (3) a second wall; and
      (4) more than one nozzle in the second wall for ejecting the aromatizer solution from the reservoir to produce aromatizer fumes, the flow rate of the aromatizer solution through the more than one nozzle being regulated by a corresponding actuating element.

16. A dispenser according to claim 15 having at least two piezoelectric crystals, the reservoir wall containing at least two nozzles, the piezoelectric crystals being arranged opposite respective nozzles, so that flow through each nozzle is controlled by a pressure pulse from the corresponding piezoelectric crystal.

17. A dispenser according to claim 15, the diameter of the nozzles in the reservoir wall ranging from 10 to 70 µm.

18. A dispenser according to claim 15, the distance between the nozzles exceeding 50 µm.

* * * * *

UNITED STATES PATENT AND TRADEMARK OFFICE
CERTIFICATE OF CORRECTION

| | | |
|---|---|---|
| PATENT NO. | : 7,077,335 B2 | |
| APPLICATION NO. | : 10/492902 | |
| DATED | : July 18, 2006 | |
| INVENTOR(S) | : Anatoly Viktorovich Golubev et al. | |

It is certified that error appears in the above-identified patent and that said Letters Patent is hereby corrected as shown below:

On the title page item [75],

Delete "Mikhail Alexandrovich Gluyansky" and insert -- Mikhail Alexandrovich Gulyansky --.

Delete "Evgeny Gennadievich Krasheninnixov" and insert -- Evgeny Gennadievich Krasheninnikov --.

Col. 2, line 16, after the word "unit" insert -- volume of a gaseous medium, for example the air. --.

Col. 2, lines 17 and 18, delete "This object is solved in accordance with the present invention by".

Col. 4, line 12, delete "S" and insert -- 5 --.

Col. 4, line 14, delete "S" and insert -- 5 --.

Col. 4, line 43, delete "vessel, in" and insert -- vessel. In --.

Col. 5, line 2, delete "element it The" and insert -- element 11. The --.

Col. 7, lines 6 and 7, delete "($10^{-5}$ - $10^{-1}$ g/sec)" and insert -- $10^{-5}$ - $10^{-1}$ g/sec --.

Col. 7, line 9, delete "($10^{11}$ - $^{1016}$ $cm^{-3}$)" and insert -- $10^{11}$ - $10^{16}$ $cm^{-3}$ --.

Col. 7, line 44, delete "reservoir." and insert -- reservoir, --.

UNITED STATES PATENT AND TRADEMARK OFFICE
CERTIFICATE OF CORRECTION

PATENT NO. : 7,077,335 B2
APPLICATION NO. : 10/492902
DATED : July 18, 2006
INVENTOR(S) : Anatoly Viktorovich Golubev et al.

It is certified that error appears in the above-identified patent and that said Letters Patent is hereby corrected as shown below:

Col. 8, line 14, delete "elements. the" and insert -- elements, the --.

Col. 8, line 45, insert -- (2) -- before "more than one plezoelectric crystal in the reservoir for"

Signed and Sealed this

Twenty-sixth Day of December, 2006

JON W. DUDAS
*Director of the United States Patent and Trademark Office*